(12) United States Patent
Comor et al.

(10) Patent No.: US 11,250,964 B2
(45) Date of Patent: Feb. 15, 2022

(54) SYSTEM FOR THE IRRADIATION OF A TARGET MATERIAL

(71) Applicant: Ion Beam Applications S.A., Louvain-la-Neuve (BE)

(72) Inventors: Jozef Comor, Belgrade (RS); Jean-Michel Geets, Louvain-la-Neuve (BE); Benoît Nactergal, Louvain-la-Neuve (BE)

(73) Assignee: ION BEAM APPLICATIONS S.A., Louvain-la-Neuve (BE)

( * ) Notice: Subject to any disclaimer, the term of this patent is extended or adjusted under 35 U.S.C. 154(b) by 0 days.

(21) Appl. No.: 16/504,760

(22) Filed: Jul. 8, 2019

(65) Prior Publication Data

US 2020/0043621 A1 Feb. 6, 2020

(30) Foreign Application Priority Data

Aug. 6, 2018 (EP) .................................... 18187472

(51) Int. Cl.
*G21G 1/00* (2006.01)
*A61N 5/10* (2006.01)
(Continued)

(52) U.S. Cl.
CPC ......... *G21G 1/0005* (2013.01); *A61N 5/1042* (2013.01); *G21G 1/10* (2013.01); *G21K 1/10* (2013.01)

(58) Field of Classification Search
None
See application file for complete search history.

(56) References Cited

U.S. PATENT DOCUMENTS

2007/0297554 A1* 12/2007 Lavie .................. G21G 1/10
376/190
2018/0043188 A1 2/2018 Abbasi

FOREIGN PATENT DOCUMENTS

| EP | 1 717 819 | 11/2006 |
| WO | WO-2013/159201 | 10/2013 |
| WO | WO-2018/106681 | 6/2018 |

OTHER PUBLICATIONS

Chai, J.S. et al. "Operation Experience of KCCH Cyclotron for 10 years and Prospect of Cyclotron in Korea," *Proceedings of the 14th International Conference on Cyclotrons and their Applications*, Cape Town, South Africa, Jan. 1, 1997; pp. 508-511.

(Continued)

*Primary Examiner* — Xiaoyun R Xu
(74) *Attorney, Agent, or Firm* — Finnegan, Henderson, Farabow, Garrett & Dunner LLP

(57) ABSTRACT

A capsule for the transfer of a target material in a conveying system between a target irradiation station and a collecting station comprising: a beamline channel for the passage of an energetic beam irradiating the target material, a target holder holding the target material or a substrate backing the target material at a glancing angle with respect to the beamline channel axis, a degrader foil positioned across the beamline channel for degrading an energy of the energetic beam upstream of the target material, a target cooling inlet and a target cooling outlet for passage of a cooling fluid in a target cooling duct in a vicinity of the target holder such that the target material can be cooled during an irradiation, and a degrader foil cooling inlet and a degrader foil cooling outlet for passage of a cooling gas in a vicinity of the degrader foil.

15 Claims, 6 Drawing Sheets

(51) Int. Cl.
    *G21K 1/10*         (2006.01)
    *G21G 1/10*         (2006.01)

(56)         References Cited

OTHER PUBLICATIONS

Spellerberg, S. et al. (1998). "Production of $^{55}$Co and $^{57}$Co via Proton Induced Reactions on Highly Enriched $^{58}$Ni," *Appl. Radiat. Isot.*, Jan. 1, 1998, vol. 49, No. 12; pp. 1519-1522.
Burgerjon, J.J. et al. "A High-Power Target System for Radioisotope Production," *Proceedings of the Eleventh International Conference on Cyclotrons and their Applications*, Tokyo, Japan, Jan. 1, 1987; pp. 634-637.
Extended European Search Report issued in corresponding European Patent Application 18187472.8 dated Feb. 20, 2019.

\* cited by examiner

SYSTEM FOR THE IRRADIATION OF A TARGET MATERIAL

CROSS-REFERENCE TO RELATED PATENT APPLICATIONS

This application claims priority of European Application No. 18187472.8, filed Aug. 6, 2018, which is hereby incorporated by reference in its entirety.

TECHNICAL FIELD

The present disclosure relates to a system for the transfer of a target material between a target irradiation station wherein the target material is irradiated by an energetic beam, such as for example a particle beam, and a collecting facility wherein the irradiated target material is collected, such as for example a hot cell in a system for the production of radionuclides.

BACKGROUND

Irradiation of target materials by an energetic beam is used in many modern applications. For example, radionuclides have long been produced by cyclotron irradiation of target materials with a medium- or low-energy (5-30 MeV) beam for medical applications. Radionuclides have many important industrial and scientific uses, including tracers. By reactions with appropriate non-radioactive precursors, radiodrugs are synthesized and, when administered in the human body, permit diagnosis and therapy monitoring by Positron Emission Tomography (PET), especially in the treatment of tumors. Some radiodrugs can have therapeutic effect as well.

Document EP 1 717 819 discloses a system for automatically producing radionuclides. In the system disclosed, a cylindrical target carrier, or capsule, comprising a partition wall defining two open cylindrical cavities is disclosed. One of the cylindrical cavities is used to house the target material for irradiation. In the system disclosed, the capsule is used as a shuttle between an irradiation unit where the target material carried by the capsule is irradiated, and a hot cell wherein the electrodeposition and the electrodissolution of the target material can take place thanks to an electrolytic cell. A pneumatic transfer system is arranged to transfer the capsule between the hot cell and the irradiation unit. A purifying system is also present and is used in order to purify the acid solution comprising the radionuclide obtained from the electrodissolution step. In this system, the irradiation takes place in an irradiation unit which receives a particle beam from a cyclotron. In the case that different radionuclides need to be produced or when target materials with different thicknesses are used in this system, the energy of the particle beam irradiating the target material may be varied. This can be done by using a more complex accelerator which can deliver a beam with a variable energy. When the accelerator can only deliver the particle beam at a fixed energy, the energy of the beam irradiating the target material can still be varied by using a degrader foil positioned across the beamline in the irradiating unit. By switching between different degrader foils, the energy of the beam obtained from a fixed energy cyclotron can consequently be tuned so as to irradiate the target material with the appropriate energy level. Switching between different degrader foils is however an awkward procedure which involves a shutting down the system, with obvious adverse economic implications, and accessing the target irradiation station, causing a radiation exposure of the maintenance staff.

SUMMARY

The present disclosure provides a system for automatically producing radionuclides with an increased flexibility for varying the energy of the beam irradiating the target material.

The disclosure concerns a capsule for the transfer of a target material in a conveying system between a target irradiation station and a collecting station, such as a hot cell, comprising:
- a beamline channel extending along a beamline channel axis for the passage of an energetic beam irradiating the target material,
- a target holder for holding the target material or a substrate backing the target material at a glancing angle with respect to the beamline channel axis,
- a housing for enclosing the target holder, the housing being openable such that the target material can be inserted in or removed from the target holder when the housing is opened,
- at least one degrader foil positioned across the beamline channel, for degrading an energy of the energetic beam upstream of the target material,
- at least one target cooling inlet and at least one one target cooling outlet for passage of a cooling fluid in a cooling duct in a vicinity of the target holder such that the target material can be cooled during an irradiation, and
- at least one degrader foil cooling inlet and at least one degrader foil cooling outlet for the passage of a cooling gas in a vicinity of the at least one degrader foil.

The disclosure also concerns a system for the irradiation of a target material in a target irradiation station and the transfer of the irradiated target material between the target irradiation station and a collecting facility, such as a hot cell, comprising:
- at least one capsule described above,
- a receiving station located in the collecting facility,
- the target irradiation station for receiving the energetic beam from a beamline along a beamline axis, and
- a conveying system comprising a transfer tube for conveying at least one capsule between the receiving station and the target irradiation station, wherein
the conveying system comprises a first terminal located in the target irradiation station,
the target irradiation station comprises:
- an irradiation unit for irradiation of the target material, a first actuator for a transfer of a capsule between the first terminal and the irradiation unit and a second actuator for locking the transferred capsule in an irradiation position wherein the beamline channel axis of the transferred capsule is aligned and connected with the beamline,
- a collimator for narrowing the energetic beam from the beamline,
- at least one target cooling inlet duct and at least one target cooling outlet duct being in fluid communication with the target cooling inlet and the target cooling outlet of the transferred capsule when the transferred capsule is locked in the irradiation position, and
- at least one degrader foil cooling inlet duct and at least one degrader foil cooling outlet duct being in fluid communication with the degrader foil cooling inlet and the degrader foil cooling outlet of the transferred capsule when the transferred capsule is locked in the irradiation position, and the receiving station is connected to the transfer tube as a second terminal of the conveying system, the receiving station being openable such that the at least one capsule can be extracted from the receiving station.

BRIEF DESCRIPTION OF THE DRAWINGS

These and further aspects of the disclosure will be explained in greater detail by way of example and with reference to the accompanying drawings in which.

The figures are not drawn to scale.

DETAILED DESCRIPTION

Figure 1:
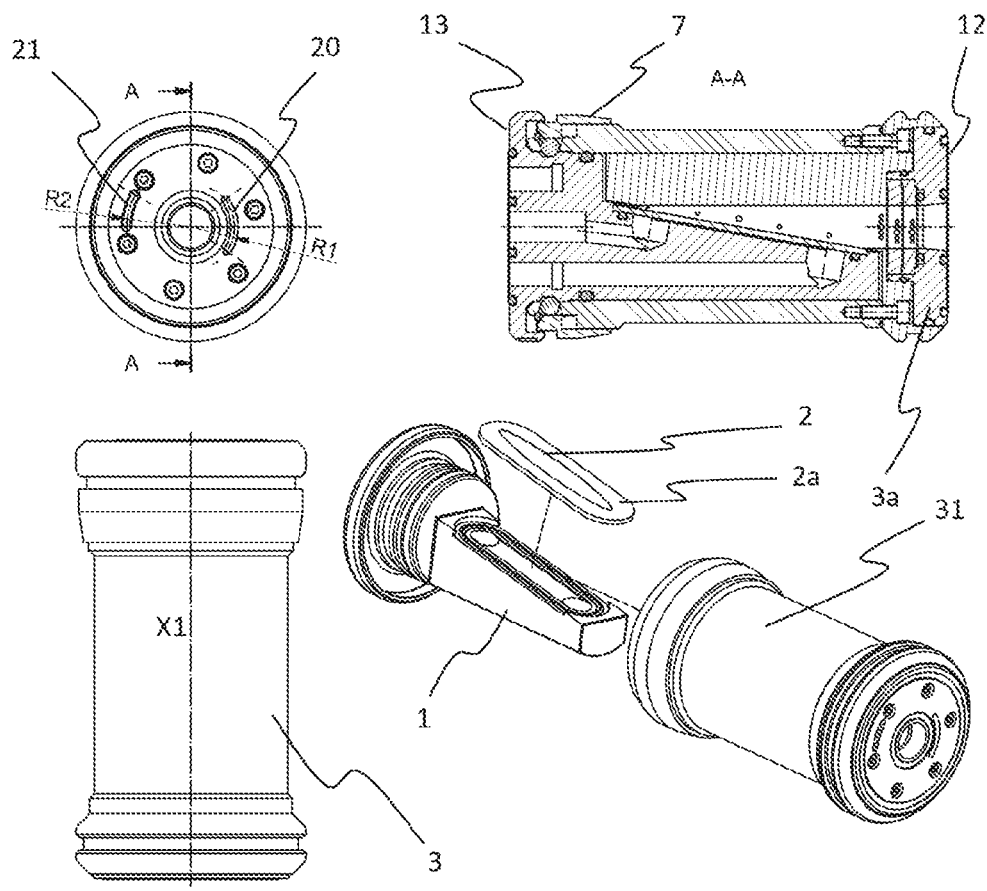
FIG. 1 shows a capsule for a system according to the present disclosure.
Figure 2:
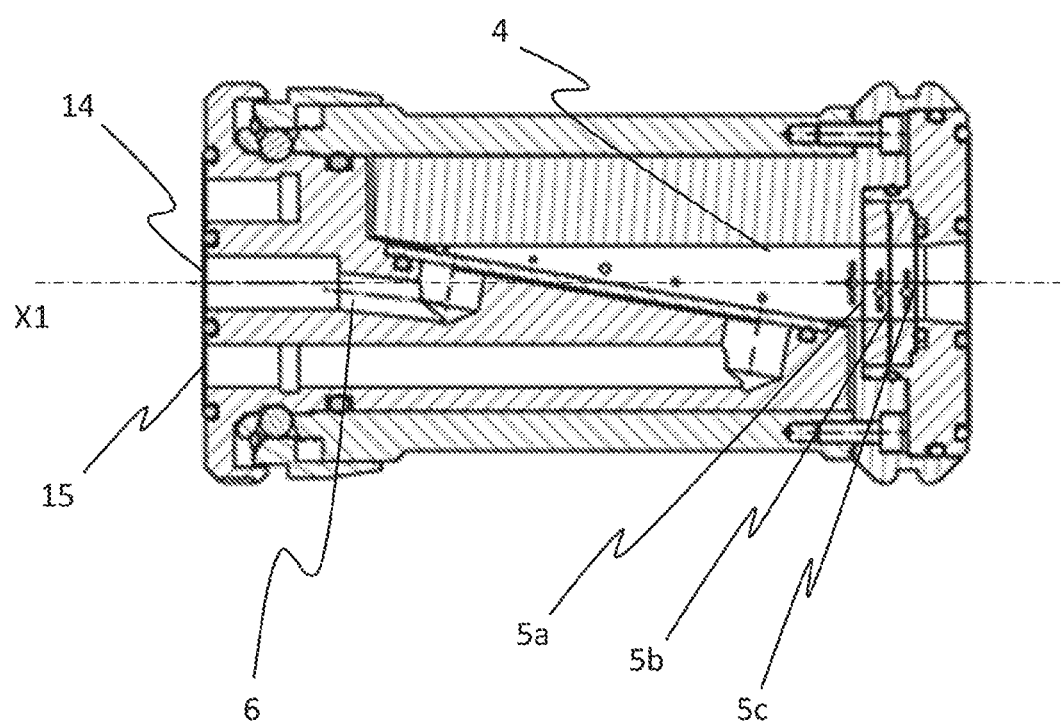
FIG. 2 is an enlarged sectional view of the capsule according to FIG. 1.

FIGS. 1 and 2 show an example of a capsule for the transfer of a target material 2 for use in a conveying system between a target irradiation station and a collecting station, such as a hot cell.

The capsule comprises:
- a beamline channel 4 extending along a beamline channel axis X1 for the passage of an energetic beam irradiating the target material 2,
- a target holder 1 for holding the target material 2 or a substrate 2a backing the target material 2 at a glancing angle with respect to the beamline channel axis X1,
- a housing 3 for enclosing the target holder 1, the housing 3 being openable such that the target material 2 can be inserted in or removed from the target holder 1 when the housing 3 is opened,
- at least one degrader foil 5a, 5b, 5c positioned across the beamline channel 4, for degrading an energy of the energetic beam upstream of the target material 2,
- at least one target cooling inlet 14 and at least one one target cooling outlet 15 for passage of a cooling fluid in a cooling duct 6 in a vicinity of the target holder 1 such that the target material 2 can be cooled during an irradiation, and
- at least one degrader foil cooling inlet 20 and at least one degrader foil cooling outlet 21 for the passage of a cooling gas in a vicinity of the at least one degrader foil 5a, 5b, 5c.

The energetic beam to be received in the capsule for irradiating the target material 2 is typically a particle beam, like a proton beam, but may also be an electromagnetic radiation, like gamma rays. Such kinds of energetic beams are used in applications for the production of radionuclides by (photo)nuclear reactions.

In FIGS. 1 and 2, the target material 2 is backed by a substrate 2a. Such target material 2 backed by a substrate 2a can be obtained by a chemical process wherein the target material 2 is electrodeposited on the substrate 2a. In another embodiment the target material can be melted or pressed into an appropriate cavity in the substrate. Alternatively, when it is not backed by a substrate, the target material 2 can be directly held by the target holder 1. Typical examples of common targets are enriched or natural nickel electrodeposited on silver or gold or gold plated copper substrates, enriched or natural thallium on copper substrate, enriched or natural zinc on copper or gold plated copper substrate, alloys of enriched or natural gallium and nickel on copper or gold plated copper, enriched or natural antimony on copper or gold plated copper substrate, enriched or natural tellurium oxide melted into a cavity in platinum or iridium substrate, enriched or natural strontium oxide pressed into a cavity in platinum or iridium substrate, natural yttrium foil fixed by a fixing ring into a cavity in platinum or iridium substrate, sheets or foils of metals without substrate, etc.

The target holder 1 is configured to receive the target material 2 and to stabilize it at a glancing angle with respect to the beamline channel axis X1. The glancing angle is in a range between 10° and 90° wherein a glancing angle of 90° corresponds to a target material 2 perpendicular to the beamline axis X1. A glancing angle lower than 90° increases the effective thickness of the target material exposed to the irradiation, which ultimately allows increasing the yield of the radionuclides production while keeping constant the actual thickness of the target material. A glancing angle lower than 90° also increases the effective surface area of the target exposed to the beam reducing the average beam current density and thereby increasing the beam current acceptance of the target and consequently the yield.

In FIGS. 1 and 2, the capsule has a tubular lateral wall defined by a geometry of revolution around the beamline channel axis X1 and is closed by a front end 12 and a back end 13. The housing 3 is a sheath enclosing the different components of the capsule. The housing 3 has a protective function for the target material 2 and can be made up of any suitable material, e.g. aluminium or aluminium alloys, titanium or titanium alloys, niobium or niobium alloys, etc.

The housing 3 is openable such that the target material 2 can be inserted or removed from the target holder 1 by a human or robotic operator, typically in a shielded nuclear radiation containment chamber (the so-called "hot cell"). In this regard, the housing 3 may comprise a main body 31 and a closing lid 7. The closing lid 7 may be coaxially fastenable to the main body 31 with respect to the beamline axis X1 so as to form the back end 13 of the capsule. The target holder 1 may be rigidly coupled to the closing lid 7 so that when the closing lid 7 is fastened to the main body 31, the target holder 1 is inserted into the main body 1 at the glancing angle. Alternatively, when the housing does not comprise a main body 31 and a closing lid 7, the housing 3 may comprise a slide system or door such that the housing is openable and the target material 2 may be accessed.

The at least one degrader foil 5a, 5b, 5c positioned across the beamline channel 4 of the capsule allows degrading the energy of the energetic beam received in the capsule such that the energy level may be reached when the beam hits the target material 2. When the beam delivered to the capsule has a fixed energy, the energy of the beam downstream of the beam generator may be tuned. The number, thickness, and material of the degrader foils that are included in the capsule depend on the beam energy level delivered by the beam generator and on the required beam energy level to be delivered on the target material 2. In FIGS. 1 and 2, the capsule comprises three degrader foils 5a, 5b, 5c. In other embodiments, the capsule may comprise only one or two degrader foils, or alternatively more than three degrader foils. In the embodiment of FIGS. 1 and 2, the degrader foils are made of aluminium and have a width of 0.25 mm. Any material of any width with a suitable energy degradation power may however be used.

The presence of degrader foils in the capsule according to the disclosure allows for the reduction of the ionising radiation dose received by the operators during the maintenance of the target station. The energy degrader foils are activated during the operation of the target station, hence they are the strongest source of ionizing radiation induced in the target station other than the target and the substrate. Since the energy degrader foils are part of the capsule, they may be removed from the target station together with the irradiated target after every irradiation. Hence, the only activated parts remaining in the vicinity of the target station are the collimators and beam stops along the beamline.

The degrader foils 5a, 5b, 5c may be removably mounted on the capsule so as to be replaceable. This allows the degrader foils 5a, 5b, 5c to be replaced, for example, after a predetermined number of irradiations, or alternatively when a new target material 2 requiring a different energy degradation power is irradiated. The degrader foils 5a, 5b, 5c may also be mounted on a support 3a being detachable from the rest of the housing 3. In such configuration, the degrader foils 5a, 5b, 5c may be changed by removing the support 3a and by mounting a new support 3a on the capsule.

The at least one cooling inlet 14 and at least one target cooling outlet 15 for the passage of a cooling fluid in a cooling duct 6 in the vicinity of the target holder 1 may be located in the back end 13 of the capsule. In FIGS. 1 and 2, the target cooling inlet 14 is a circular inlet aligned with the beamline channel axis X1, while the target cooling outlet 15 is an annular outlet located around the beamline channel axis X1. The cooling duct 6 is a passage in the capsule connecting the target cooling inlet 14 to the target cooling outlet 15. The function of the cooling duct 6 is to evacuate the heat generated during the irradiation from the target material 2. The cooling duct 6 circulates a cooling fluid, such as cooling water, or any other suitable fluid with high boiling point, high heat capacity and high heat conductivity near the target material 2. In FIGS. 1 and 2, the cooling duct 6 is configured to bring the cooling fluid in contact with the substrate 2a backing the target material 2. In other embodiments, the cooling duct 6 may be configured such that the cooling fluid is brought near the substrate 2a without contacting it. In these embodiments, the cooling duct 6 comprises a portion separated from the substrate 2a by a thin layer of thermally conductive material.

The energetic beam received by the capsule may also generate a heating of the degrader foils 5a, 5b, 5c. In order to limit the thermal increase in the degrader foils, a cooling fluid may be brought in the vicinity of the at least one degrader foil 5a, 5b, 5c. As represented in FIGS. 1 and 2, a degrader foil cooling inlet 20 and a degrader foil cooling outlet 21 may be configured to allow the passage of a cooling fluid tangentially to the degrader foils 5a, 5b, 5c. As it will spread in the beamline channel 4 during the irradiation, the cooling fluid may be an inert substance, such as a noble gas. In FIGS. 1 and 2, the degrader foil cooling inlet 20 is an arc shaped inlet with a radius R1 located in the front end 12 of the capsule. The degrader foil cooling outlet 21 is an arc shaped outlet also located in the front end 12 of the capsule, but with a radius R2 different from R1.

In the capsule represented in FIGS. 1 and 2, the degrader foil 5c and target holder 1 define a closed cavity in the beamline channel 4. In this configuration, the contamination of the target irradiation station and of the beamline by the cooling fluid circulated in the beamline channel 4 is prevented because the cooling fluid does not leak outside of the closed cavity in the capsule. In addition, the circulation of the cooling fluid in the beamline channel 4 may be forced tangentially to the front face of the target material, and enhance the heat removal from the target, which is particularly important for target materials with low heat conductivity.

The presence of the degrader foils 5a, 5b, 5c embedded in the capsule allows tuning the energetic beam upstream of the target material 2 without having to switch between degrader foils located in the target irradiation station 10. The use of the capsule in a system for producing radionuclides is consequently advantageous. With the capsule according to the disclosure, different target materials 2 requiring different beam energy levels may be irradiated successively without using a beam generator with a variable energy level and without accessing the target irradiation station 10.

Figure 3:
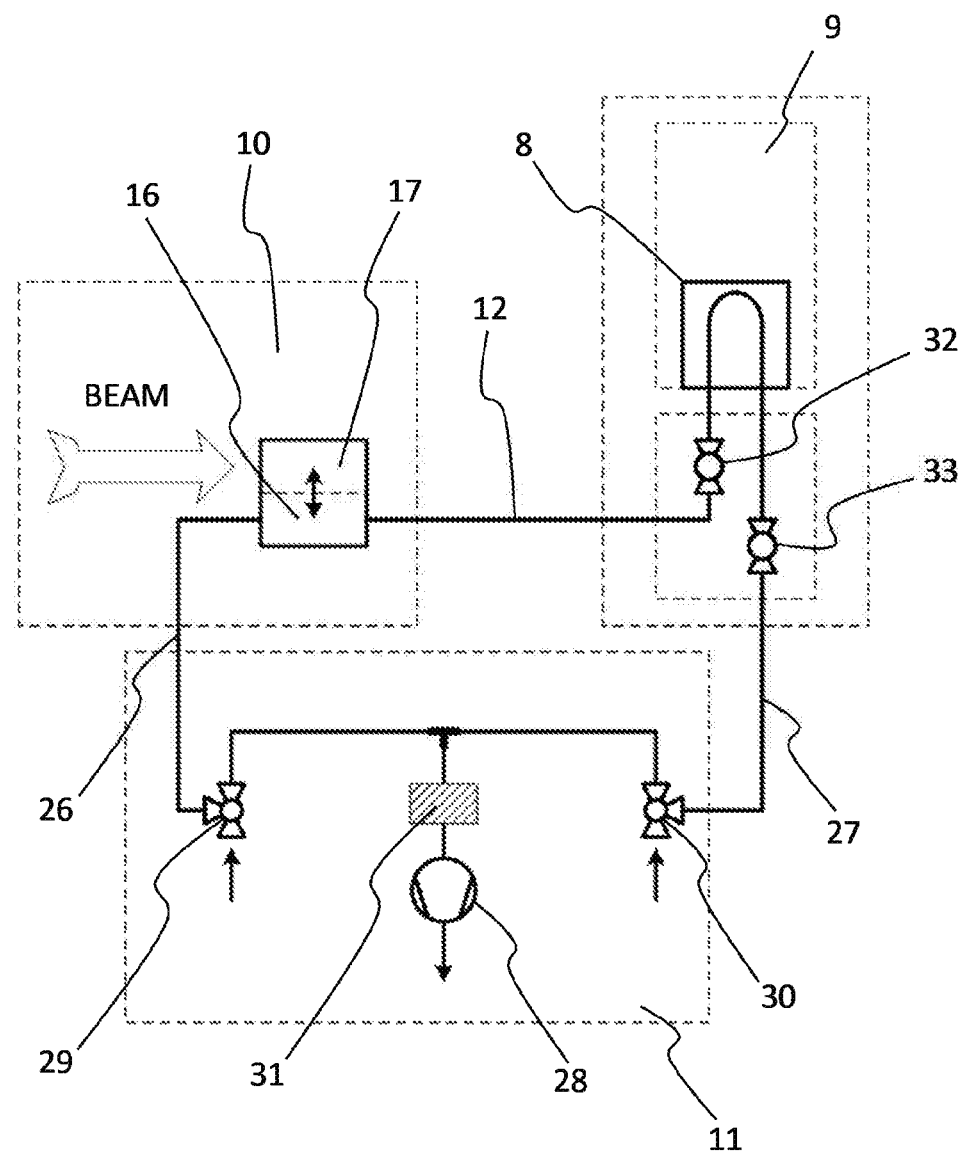
FIG. 3 is a schematic view of a system according to the present disclosure.
Figure 4:
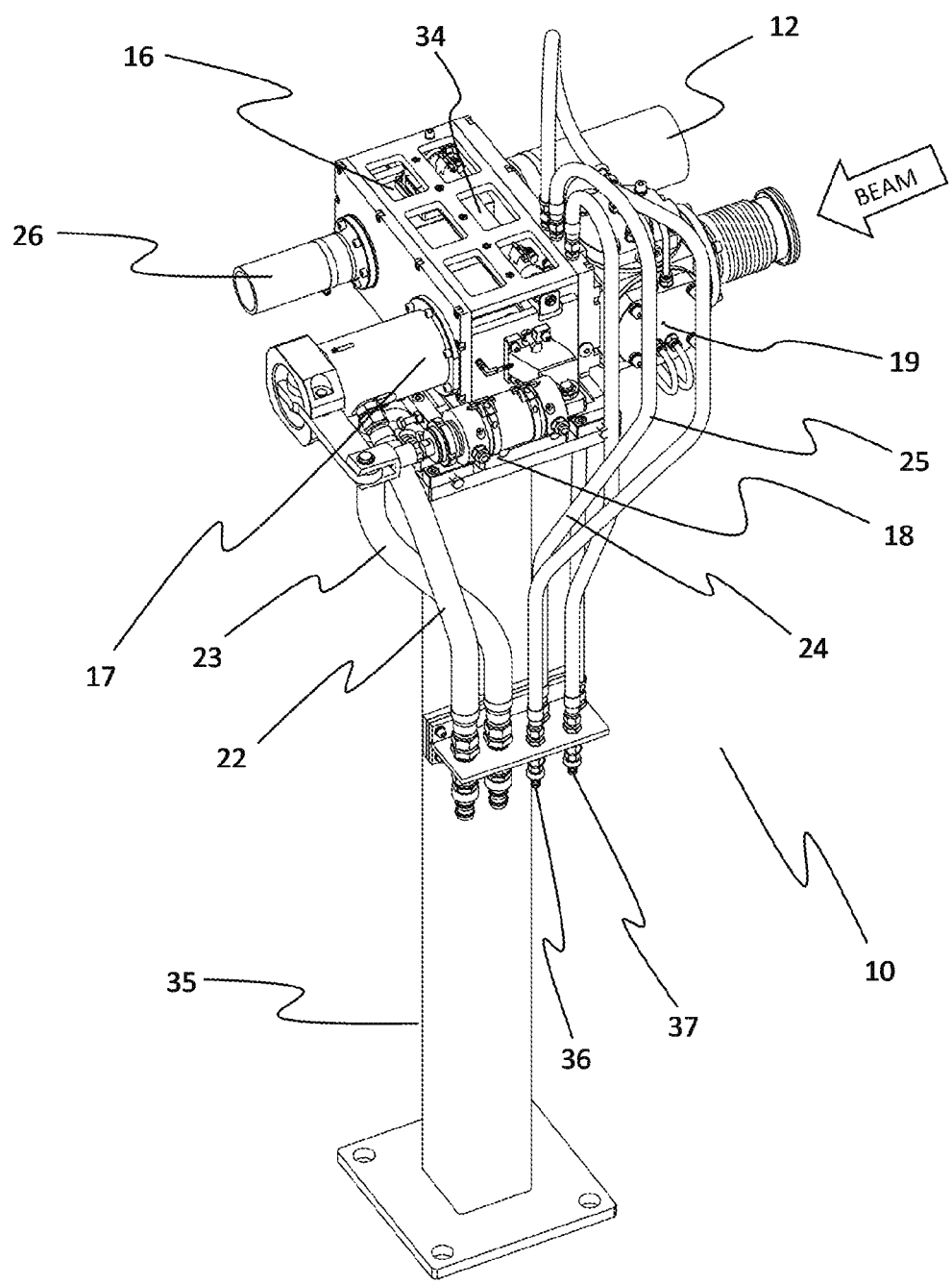
FIG. 4 shows the target irradiation station of a system according to the present disclosure.

As represented in FIG. 3, the present disclosure also relates to a system for the irradiation of a target material in a target irradiation station 10 and the transfer of the irradiated target material between the target irradiation station 10 and a collecting facility, such as a hot cell 9. The system comprises:
  at least one capsule described above,
  a receiving station 8 located in the collecting facility 9,
  the target irradiation station 10, as represented in FIG. 4,
    for receiving the energetic beam from a beamline along a beamline axis, and
  a conveying system 11 comprising a transfer tube 12 for conveying at least one capsule between the receiving station 8 and the target irradiation station 10,
  wherein
  the conveying system 11 comprises a first terminal 16 located in the target irradiation station 10,
  the target irradiation station 10 comprises:
    an irradiation unit 17 for irradiation of the target material 2,
    a first actuator 34 for a transfer of a capsule between the first terminal 16 and the irradiation unit 17 and a second actuator 18 for locking the transferred capsule in an irradiation position wherein the beamline channel axis X1 of the transferred capsule is aligned and connected with the beamline,
    a collimator 19 for narrowing the energetic beam from the beamline, at least one target cooling inlet duct 22 and at least one target cooling outlet duct 23 being in fluid communication with the target cooling inlet 14 and the target cooling outlet 15 of the transferred capsule when the transferred capsule is locked in the irradiation position, and
    at least one degrader foil cooling inlet duct 24 and at least one degrader foil cooling outlet duct 25 being in fluid communication with the degrader foil cooling inlet 20 and the degrader foil cooling outlet 21 of the transferred capsule when the transferred capsule is locked in the irradiation position, and
  the receiving station 8 is connected to the transfer tube 12 as a second terminal of the conveying system 11, the receiving station 8 being openable such that the at least one capsule can be extracted from the receiving station 8.

In the system represented in FIG. 3, the conveying system 11 is a vacuum pneumatic conveying system. Such system comprises a first suction tube 26 in fluid communication with the transfer tube through the first terminal 16 in the target irradiation station 10. The conveying system 11 also comprises a second suction tube 27 in fluid communication with the transfer tube 12 through the receiving station 8 ("second terminal"). The suction tubes 26, 27 are connected to an air blower 28 and to the atmosphere through three-way valves 29 and 30. A HEPA filter 31 may also be included between the air blower 28 and the three-way valves 29 and 30.

The principle of operation of the conveying system is the following. When the capsule needs to be transferred from the collecting facility 9 to the target irradiation station 10, the atmosphere port of the first three-way valve 29 is closed while the first suction tube 26 is set in fluid communication with the blower 28. On the other hand, the air blower port of the second three-way valve 30 is closed while the second suction tube 27 is set in fluid communication with the atmosphere. The air is consequently sucked out of the first suction tube 26 through the air blower 28. This depression in the suction tube 26 generates a motion of the capsule in the transfer tube 12 from the collecting facility 9 to the target irradiation station 10 and at the same time an air suction from the atmosphere into the second suction tube 27. When the capsule needs to be transferred from the target irradiation station 10 to the collecting facility 9, the atmosphere port of the second three-way valve 30 is closed while the second suction tube 27 is set in fluid communication with the blower 28. On the other hand, the air blower port of the first three-way valve 29 is closed while the suction tube 26 is set in fluid communication with the atmosphere. The air is consequently sucked out of the second suction tube 27 through the air blower 28. This depression in the suction tube 27 generates a motion of the capsule in the transfer tube 12 from the target irradiation station 10 to the collecting facility and at the same time an air suction from the atmosphere into the first suction tube 26.

As represented in FIG. 3, the system may comprise two additional valves 32, 33, such as ball valves, in the collecting facility 9. The first valve 32 is positioned across the transfer tube 12 and the second valve 33 is positioned across the second suction tube 27. In this arrangement, the receiving station 8 becomes consequently an airlock in the hot cell 9. These valves 32, 33 may be kept closed when a capsule is extracted or placed in the receiving station 8. This operation may ensure that the atmosphere of the hot cell 9 is not disturbed by the air used for the transfer of the capsules and that the potentially contaminated atmosphere of the hot cell 9 will not enter the air stream of the conveying system 11. When a capsule needs to be transferred between the hot cell 9 and the target irradiation station 10, the valves 32, 33 may be opened such that the conveying system 11 can be operated as described above.

Figure 5:
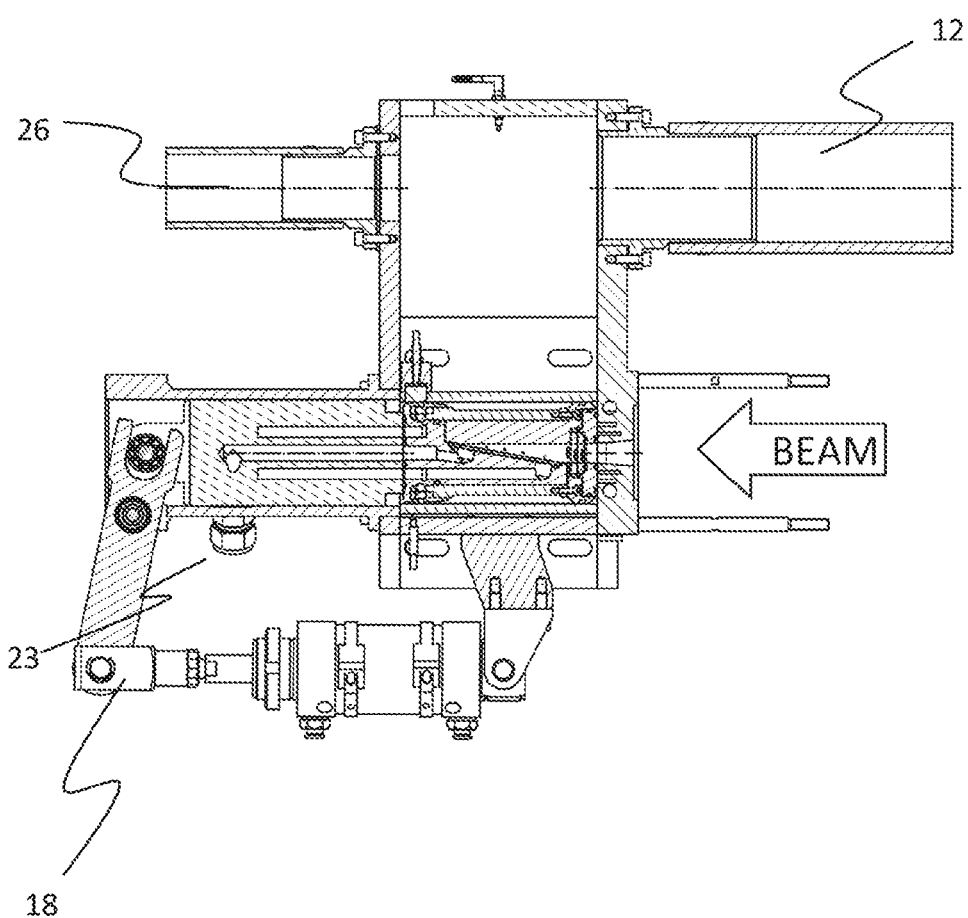
FIG. 5 shows a sectional view of the target irradiation station according to FIG. 4, with a capsule locked in an irradiation position.

An example of a target irradiation station 10 of a system according to disclosure is disclosed in more details in FIGS. 4 and 5. The target irradiation station 10 is mounted on a mounting stand 35 through a positioning mechanism, which allows for a precise alignment of the irradiation unit relative to the beam. Besides the elements already described, the target irradiation station 10 can also comprise a cooling system for the collimator 19. Such cooling system comprises a collimator cooling inlet duct 36 and a collimator cooling outlet duct 37.

As represented in FIGS. 4 and 5, the target irradiation station 10 comprises two actuators 34 and 18 for positioning and locking the capsules. When the capsule is received in the first terminal 16 of the target irradiation station 10, the first actuator 34 transfers the capsule to the irradiation unit 17. By the action of the second actuator 18 the capsule is locked in its irradiation position. The irradiation position of the capsule in the irradiation unit 17 is a position of the capsule wherein the beamline channel axis X1 is aligned and connected with the beamline. Furthermore, the target cooling inlet duct 22 and the target cooling outlet duct 23 are in fluid communication with the target cooling inlet 14 and the target cooling outlet 15 of the capsule, and the degrader foil cooling inlet duct 24 and the degrader foil cooling outlet duct 25 are in fluid communication with the degrader foil cooling inlet 20 and the degrader foil cooling outlet 21 of the capsule.

In an alternative embodiment of the system, the target cooling inlet duct 22 of the target irradiation station 10 may be configured such that it is in fluid communication with the target cooling inlet 14 of the capsule irrespective of the relative angular orientation between the capsule and the irradiation unit 17 with respect to the beamline channel axis X1 when the capsule is locked in the irradiation position. Similarly, the target cooling outlet duct 23 of the target irradiation station 10 may be configured such that it is in fluid communication with the target cooling outlet of the capsule irrespective of the relative angular orientation between the capsule and the irradiation unit 17 with respect to the beamline channel axis X1 when the capsule is locked in the irradiation position. In this configuration, the target cooling system is operational at any angular orientation of the capsule in the irradiation unit 17 with respect to the beamline channel axis X1. This reduces the task complexity of the actuators 18 and 34, which may not need to measure the angular orientation of the capsule in the first terminal 16 and may not need to rotate the capsule at a particular angle with respect to the beamline channel axis X1 when locking the capsule in its irradiation position.

In the capsule represented in FIGS. 1 and 2, the target cooling inlet 14 is a circular inlet located in the back end 13 of the capsule and is aligned with the beamline channel axis X1, and the target cooling inlet duct 22 of the target irradiation station 10 has an end portion located on the beamline axis and with a circular shape having a radius matching the radius of the circular target cooling inlet 14 of the capsule. Similarly, as represented in FIGS. 1 and 2, when the target cooling outlet 15 of the capsule is an annular outlet in the back end 13 of the capsule and is located around the beamline channel axis X1, the target cooling outlet duct 23 of the target irradiation station 10 has an end portion with an annular outlet around the beamline axis and having a radius matching the radius of the target cooling outlet 15. In this example of configuration, the target cooling system is operational irrespective of the relative angular orientation between the capsule and the irradiation unit 17 with respect to the beamline channel axis X1 when the capsule is locked in the irradiation position.

In an alternative embodiment of the system, the degrader foil cooling inlet duct 24 of the target irradiation station 10 may be configured such that it is in fluid communication with the degrader foil cooling inlet 20 of the capsule irrespective of the relative angular orientation between the capsule and the irradiation unit 17 with respect to beamline channel axis X1 when the capsule is locked in the irradiation position. Similarly, the degrader foil cooling outlet duct 25 of the target irradiation station 10 may be configured such that it is in fluid communication with the degrader foil cooling outlet 21 of the capsule irrespective of the relative angular orientation between the capsule and the irradiation unit 17 with respect to the beamline channel axis X1 when the capsule is locked in the irradiation position. In this configuration, the degrader cooling system may be operational at any angular orientation of the capsule in the irradiation unit 17 with respect to the beamline channel axis X1. This reduces the task complexity of the actuators 18 and 34, which may not need to measure the angular orientation of the capsule in the first terminal 16 and may not need to rotate the capsule at a particular angle with respect to the beamline channel axis X1 when locking the capsule in its irradiation position.

In the capsule represented in FIGS. 1 and 2, the degrader foil cooling inlet 20 is located in the front end 12 of the capsule and is an arc shaped inlet with a radius R1 around the beamline channel axis X1, and the degrader foil cooling inlet duct 24 of the target irradiation station 10 has an end portion with an annular shape around the beamline axis and having a radius matching the radius R1 of the arc shaped inlet 20 of the capsule. Similarly, as represented in FIGS. 1 and 2, when the degrader foil cooling outlet 21 is located in the front end 12 of the capsule and is an arc shaped outlet having a radius R2 around the beamline channel axis X1 different from the radius R1, the degrader foil cooling outlet duct 25 of the target irradiation station 10 has an end portion with an annular shape around the beamline axis and having a radius matching the radius R2 of the degrader foil cooling outlet 21.

Figure 6:
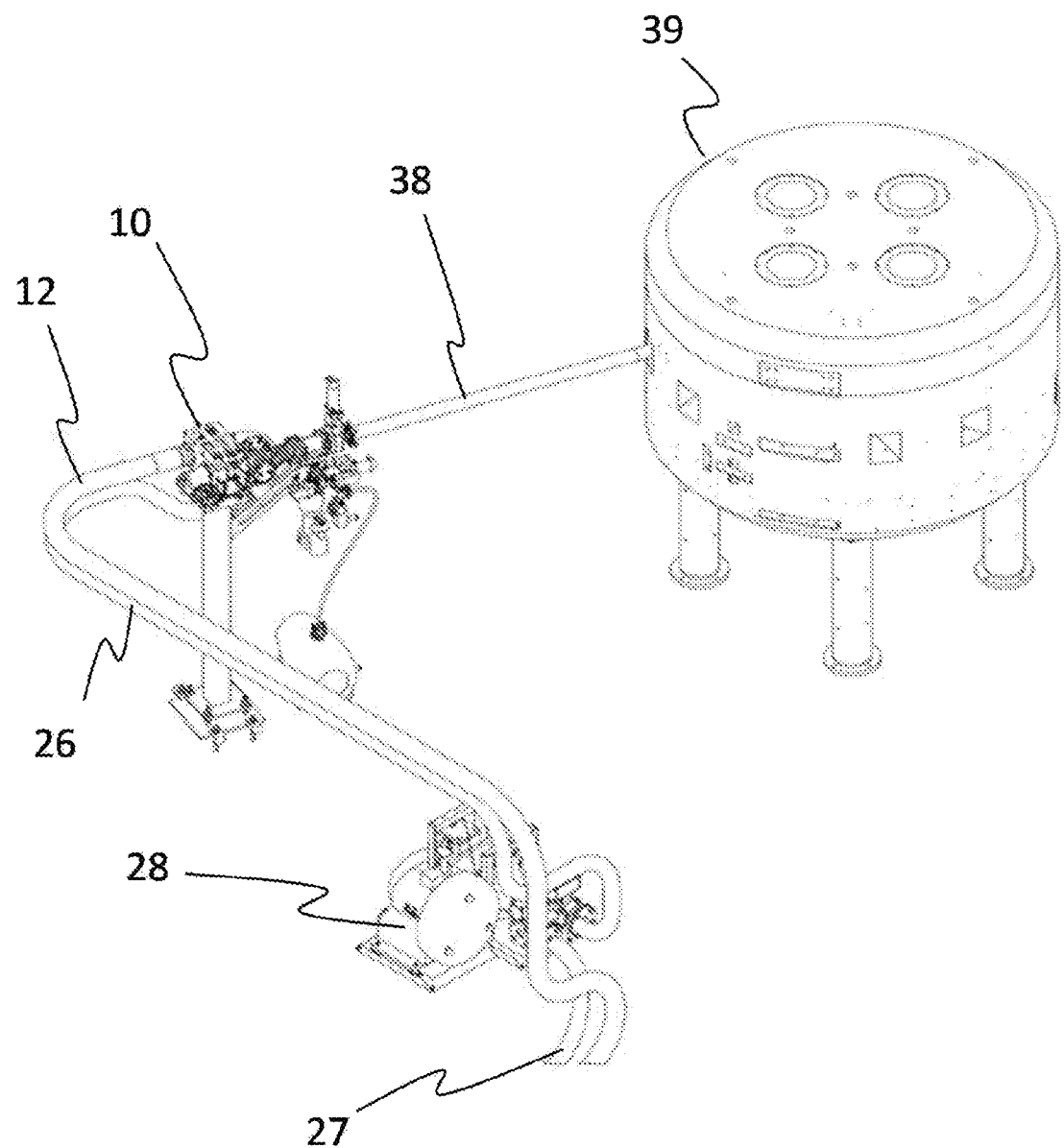
FIG. 6 is a detailed view of a part of a system according to the disclosure connected to the beamline of an energetic beam generator.

FIG. 6 represents a detailed view of a part of a system according to the disclosure connected to the beamline 38 of an energetic beam generator 39. The energetic beam generator 39 may be a particle accelerator such as a cyclotron. Alternatively, the energetic beam generator may generate electromagnetic radiation, like gamma rays.

In one embodiment, the glancing angle may be between 10 degrees and 90 degrees.

In another embodiment, the capsule may have a shape defined by a geometry of revolution around the beamline channel axis X1, the capsule comprising a front end and a back end, the beamline channel extending inside the capsule from the front end to the target holder.

In another embodiment, the target cooling inlet may be located in the back end of the capsule, the target cooling inlet being aligned with the beamline channel axis X1.

In another embodiment, the target cooling outlet may be located in the back end of the capsule, the target cooling outlet being an annular cooling outlet located around the beamline channel axis X1.

In another embodiment, the housing comprises a closing lid, wherein
  the closing lid is coaxially fastenable to the housing with respect to the beamline axis X1 so as to form a back end of the capsule,
  the target holder is rigidly coupled to the closing lid such that the target holder is inserted into the housing when the closing lid is fastened to the housing.

The target cooling duct may be configured such that the cooling fluid can be in thermal contact the target material or the substrate backing the target material held in the target holder. Furthermore, the conveying system may be a pneumatic system, or a vacuum pneumatic system.

The receiving station may be connected to the transfer tube through a gate valve such that the second terminal can be used as an airlock between the conveying system and the collecting facility.

The target cooling inlet duct and the target cooling outlet duct of the target irradiation station, as well as the target cooling inlet and the target cooling outlet of the capsule, are configured such that the target cooling inlet duct of the target irradiation station is in fluid communication with the target cooling inlet of the capsule such that the target cooling outlet duct of the target irradiation station is in fluid communication with the target cooling outlet of the capsule irrespective of the relative angular orientation between the capsule and the irradiation unit with respect to the beamline channel axis X1 when the capsule is locked in the irradiation position.

In another embodiment, the target cooling inlet of the capsule may be a circular inlet located in the back end of the capsule, with the target cooling inlet being aligned with the beamline channel axis X1. The target cooling outlet of the capsule may be located in the back end of the capsule, the target cooling outlet being an annular cooling outlet located around the beamline channel axis X1. The target cooling inlet duct of the target irradiation station may have an end portion located on the beamline axis with a circular shape having a radius matching the radius of the target cooling inlet of the capsule. The target cooling outlet duct of the target irradiation station may have an end portion located on the beamline axis with an annular outlet having a radius matching the radius of the target cooling outlet of the capsule.

In another embodiment, the degrader foil cooling inlet duct and the degrader foil cooling outlet duct of the target irradiation station, as well as the degrader foil cooling inlet and the degrader foil cooling outlet of the capsule, may be configured such that the degrader foil cooling inlet duct of the target irradiation station is in fluid communication with the degrader foil cooling inlet of the capsule and such that the at least one degrader foil cooling outlet duct of the target irradiation station is in fluid communication with the degrader foil cooling outlet of the capsule irrespective of the relative angular orientation between the capsule and the target irradiation station with respect to the beamline channel axis X1 when the capsule is locked in the irradiation position.

In another embodiment, the degrader foil cooling inlet of the capsule may be an arc shaped inlet with a radius R1 located in the front end of the capsule, and the degrader foil cooling outlet of the capsule may be an arc shaped outlet located in the front end of the capsule, with the arc shaped outlet having a radius R2 different from the radius R1. The degrader foil cooling inlet duct of the target irradiation station may have an end portion with an annular shape around the beamline axis having a radius matching the radius R1 of the arc shaped inlet of the capsule. The degrader foil cooling outlet duct of the target irradiation station may have an end portion with an annular shape around the beamline axis having a radius matching the radius R2 of the arc shaped outlet of the capsule.

The invention claimed is:

1. A capsule for the transfer of a target material in a conveying system between a target irradiation station and a collecting station, comprising:
  a beamline channel extending along a beamline channel axis for passage of an energetic beam irradiating the target material,
  a target holder for holding the target material or a substrate backing the target material at a glancing angle with respect to the beamline channel axis,
  a cylindrical housing for enclosing the target holder by encircling the target holder within the housing, the housing being openable such that the target material can be inserted in or removed from the target holder when the housing is opened,
  a degrader foil positioned across the beamline channel for degrading energy of the energetic beam upstream of the target material, a target cooling inlet and a target cooling outlet for passage of a cooling fluid in a target cooling duct in a vicinity of the target holder such that the target material can be cooled during the irradiation, and a degrader foil cooling inlet and a degrader foil cooling outlet for passage of a cooling gas in a vicinity of the degrader foil;

wherein each of the target cooling inlet, the target cooling outlet, the degrader foil cooling inlet, and the degrader foil cooling outlet is configured to be in fluid communication with the target irradiation station regardless of angular orientation between the capsule and an irradiation unit of the irradiation station with respect to the beamline channel axis.

2. The capsule according to claim 1, wherein the glancing angle is comprised between 10 degrees and 90 degrees.

3. The capsule according to claim 1, wherein the capsule has a shape defined by a geometry of revolution around the beamline channel axis, the capsule comprising a front end and a back end, and the beamline channel extending inside the capsule from the front end to the target holder.

4. The capsule according to claim 3, wherein the target cooling inlet is located in the back end of the capsule, the target cooling inlet being aligned with the beamline channel axis.

5. The capsule according to claim 3, wherein the target cooling outlet is located in the back end of the capsule, the target cooling outlet being an annular cooling outlet located around the beamline channel axis.

6. The capsule according to claim 1, wherein the housing comprises a closing lid, wherein:
the closing lid is coaxially fastenable to the housing with respect to the beamline axis so as to form a back end of the capsule, and
the target holder is rigidly coupled to the closing lid such that the target holder is inserted into the housing when the closing lid is fastened to the housing.

7. The capsule according to claim 1, wherein the target cooling duct is configured such that the cooling fluid can be in thermal contact with the target material or the substrate backing the target material held in the target holder.

8. A system for the irradiation of a target material in the target irradiation station and a transfer of the irradiated target material between the target irradiation station and a collecting facility comprising:
a capsule according to claim 1,
a receiving station located in the collecting facility,
the target irradiation station for receiving the energetic beam from a beamline along a beamline axis,
a conveying system comprising a transfer tube for conveying the capsule between the receiving station and the target irradiation station,
wherein
the conveying system comprises a first terminal located in the target irradiation station,
the target irradiation station comprises:
an irradiation unit for the irradiation of the target material,
a first actuator for a transfer of a capsule between the first terminal and the irradiation unit and a second actuator for locking the transferred capsule in an irradiation position, wherein the beamline channel axis of the transferred capsule is aligned and connected with the beamline,
a collimator for narrowing the energetic beam from the beamline, a target cooling inlet duct and a target cooling outlet duct being in fluid communication with the target cooling inlet and the target cooling outlet of the transferred capsule when the transferred capsule is locked in the irradiation position, and a degrader foil cooling inlet duct and a one degrader foil cooling outlet duct being in fluid communication with the degrader foil cooling inlet and the degrader foil cooling outlet of the transferred capsule when the transferred capsule is locked in the irradiation position, and the receiving station is connected to the transfer tube as a second terminal of the conveying system, the receiving station being openable such that the capsule can be extracted from the receiving station.

9. The system according to claim 8 wherein the conveying system is a pneumatic system.

10. The system according to claim 9 wherein the conveying system is a vacuum pneumatic system.

11. The system according to claim 8, wherein the receiving station is connected to the transfer tube through a gate valve such that the second terminal can be used as an airlock between the conveying system and the collecting facility.

12. The system according to claim 8, wherein the target cooling inlet duct and the target cooling outlet duct of the target irradiation station, as well as the target cooling inlet and the target cooling outlet of the transferred capsule, are configured such that the target cooling inlet duct of the target irradiation station is in fluid communication with the target cooling inlet of the transferred capsule and such that the target cooling outlet duct of the target irradiation station is in fluid communication with the target cooling outlet of the transferred capsule irrespective of a relative angular orientation between said the transferred capsule and the target irradiation unit with respect to the beamline channel axis when the transferred capsule is locked in the irradiation position.

13. The system according to claim 12 wherein:
the target cooling inlet of the transferred capsule is a circular inlet located in a back end of the transferred capsule, the target cooling inlet being aligned with the beamline channel axis,
the target cooling outlet of the transferred capsule is located in the back end of the transferred capsule, the target cooling outlet being an annular cooling outlet located around the beamline channel axis,
the target cooling inlet duct of the target irradiation station has an end portion located on the beamline axis with a circular shape having a radius matching a radius of the target cooling inlet of the transferred capsule,
the target cooling outlet duct of the target irradiation station has an end portion located on the beamline axis with an annular outlet having a radius matching a radius of the target cooling outlet of the transferred capsule.

14. The system according to claim 8 wherein the degrader foil cooling inlet duct and the degrader foil cooling outlet duct of the target irradiation station, as well as the degrader foil cooling inlet and the degrader foil cooling outlet of the transferred capsule, are configured such that the degrader foil cooling inlet duct of the target irradiation station is in fluid communication with the degrader foil cooling inlet of the transferred capsule and such that the degrader foil cooling outlet duct of the target irradiation station is in fluid communication with the degrader foil cooling outlet of the transferred capsule irrespective of a relative angular orientation between the transferred capsule and the irradiation unit with respect to the beamline channel axis when the transferred capsule is locked in the irradiation position.

15. The system according to claim 8 wherein:
the degrader foil cooling inlet of the capsule is an arc shaped inlet with a radius R1 located in a front end of the capsule,
the degrader foil cooling outlet of the capsule is an arc shaped outlet located in the front end of the capsule, the arc shaped outlet having a radius R2 different from the radius R1,
the degrader foil cooling inlet duct of the target irradiation station has an end portion with an annular shape around the beamline axis having a radius matching the radius R1 of the arc shaped inlet of the capsule, and
the degrader foil cooling outlet duct of the target irradiation station has an end portion with an annular shape around the beamline axis having a radius matching the radius R2 of the arc shaped outlet of the capsule.

\* \* \* \* \*

UNITED STATES PATENT AND TRADEMARK OFFICE
CERTIFICATE OF CORRECTION

PATENT NO. : 11,250,964 B2
APPLICATION NO. : 16/504760
DATED : February 15, 2022
INVENTOR(S) : Jozef Comor et al.

It is certified that error appears in the above-identified patent and that said Letters Patent is hereby corrected as shown below:

On the Title Page

Item (72), in the Inventors, Line 3, "Benoît Nactergal," should read --Benoît Nactergal,--.

Item (30), in the Foreign Application Priority Data, "18187472" should read --18187472.8--.

Signed and Sealed this
Eighteenth Day of April, 2023

Katherine Kelly Vidal
*Director of the United States Patent and Trademark Office*